US009135728B2

(12) United States Patent
Fan et al.

(10) Patent No.: US 9,135,728 B2
(45) Date of Patent: Sep. 15, 2015

(54) SYSTEM AND METHOD FOR MULTI-ENERGY COMPUTED TOMOGRAPHY IMAGING

(75) Inventors: Jiahua Fan, New Berlin, WI (US); Jiang Hsieh, Brookfield, WI (US); Naveen Chandra, Waukesha, WI (US); Suresh Narayanan Narayanan, Pewaukee, WI (US); Dan Xu, Aurora, IL (US)

(73) Assignee: General Electric Company, Schenectady, NY (US)

( * ) Notice: Subject to any disclaimer, the term of this patent is extended or adjusted under 35 U.S.C. 154(b) by 662 days.

(21) Appl. No.: 13/439,245

(22) Filed: Apr. 4, 2012

(65) Prior Publication Data
US 2013/0266115 A1    Oct. 10, 2013

(51) Int. Cl.
*G06T 11/00*   (2006.01)
*A61B 6/06*    (2006.01)
*A61B 6/00*    (2006.01)
*G21K 1/02*    (2006.01)
A61B 6/03      (2006.01)
G21K 1/10      (2006.01)
H01J 35/26     (2006.01)
H01J 35/30     (2006.01)

(52) U.S. Cl.
CPC .............. *G06T 11/005* (2013.01); *A61B 6/06* (2013.01); *A61B 6/4021* (2013.01); *A61B 6/4035* (2013.01); *A61B 6/482* (2013.01); *G21K 1/025* (2013.01); *A61B 6/032* (2013.01); *A61B 6/4241* (2013.01); *A61B 6/4291* (2013.01); *A61B 6/582* (2013.01); *G06T 2211/408* (2013.01); *G21K 1/10* (2013.01); *H01J 35/26* (2013.01); *H01J 35/30* (2013.01)

(58) Field of Classification Search
CPC ...... A61B 6/06; A61B 6/4021; A61B 6/4035; A61B 6/482; A61B 6/032; G06T 2211/408
USPC ............................................................ 378/5
See application file for complete search history.

(56) References Cited

U.S. PATENT DOCUMENTS

2003/0147502 A1*  8/2003  Heismann et al. ............ 378/156
2007/0019784 A1*  1/2007  Ting ................................ 378/21

(Continued)

OTHER PUBLICATIONS

Li et al., Head and body CTDIw of dual-energy x-ray CT with fast-kVp switching, 2010, SPIE, vol. 7622, pp. 1Y-1 to 1Y-12.*
Wu et al., Monochromatic CT Image Representation via Fast Switching Dual kVp, 2009, SPIE, vol. 7258, pp. 45-1 to 45-9.*
Hsieh et al., CT Spectral Projection Imaging, 2009, 2009 IEEE Nuclear Science Symposium Conference Record, pp. 3513-3516.*

(Continued)

*Primary Examiner* — David J Makiya
*Assistant Examiner* — John Corbett
(74) *Attorney, Agent, or Firm* — Ziolkowski Patent Solutions Group, SC

(57) ABSTRACT

A CT system includes a gantry, an x-ray source, a detector, and a grating collimator that includes alternating first and second materials. The system includes a controller configured to emit a first beam of x-rays from a first focal spot and to a first detector pixel, wherein the first beam of x-rays passes along a ray and through one of the first materials of the grating collimator, and subsequently emit a second beam of x-rays from a second focal spot and to the first detector pixel, wherein the second beam of x-rays passes substantially along the ray and through one of the second materials of the grating collimator. The system includes a computer programmed to generate first and second kVp image datasets using data acquired from the first beam and second beams of x-rays, and reconstruct a basis material image of the object.

23 Claims, 8 Drawing Sheets

(56) References Cited

U.S. PATENT DOCUMENTS

| | | | |
|---|---|---|---|
| 2008/0247504 A1* | 10/2008 | Edic et al. | 378/9 |
| 2010/0172464 A1* | 7/2010 | Pavlovich et al. | 378/9 |
| 2011/0052022 A1* | 3/2011 | Xu et al. | 382/131 |

OTHER PUBLICATIONS

Kalender et al., "An Algorithm for Noise Suppression in Dual Energy CT Material Density Images," IEEE Transaction on Medical Imaging, vol. 7, No. 3, Sep. 1988, pp. 218-224.

* cited by examiner

SYSTEM AND METHOD FOR MULTI-ENERGY COMPUTED TOMOGRAPHY IMAGING

BACKGROUND

Embodiments of the invention relate generally to diagnostic imaging and, more particularly, to a system and method of acquiring multi-energy data for material decomposition.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include an anti-scatter grid or collimator for rejecting scattered x-rays at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In a given energy region relevant to medical CT, two physical processes dominate the x-ray attenuation: (1) Compton scatter and the (2) photoelectric effect. These two processes are sensitive to the photon energy and hence each of the atomic elements has a unique energy sensitive attenuation signature. Therefore, the detected signals from two energy regions provide sufficient information to resolve the energy dependence of the attenuation of the material being imaged. Furthermore, detected signals from the two energy regions provide sufficient information to determine material attenuation coefficients in terms of Compton scatter and photoelectric effect. Alternatively, the material attenuation may be expressed as the relative composition of two hypothetical materials. As understood in the art, using a mathematical change of basis, energy sensitive attenuation can be expressed in terms of two base materials, densities, effective Z number, or as two monochromatic representations having different keV. In some cases, such as in the presence of materials with K-edges in their attenuation profile, more than two basis functions may be preferred. And, as known in the art, one known method for material decomposition image reconstruction reconstructs a material basis image based on the two base materials.

A CT imaging system may therefore include an energy sensitive (ES), multi-energy (ME), and/or dual-energy (DE) CT imaging system that may be referred to as an ESCT, MECT, and/or DECT imaging system, in order to acquire data for material decomposition or effective Z or monochromatic image estimation. ESCT/MECT/DECT provides energy discrimination. For example, in the absence of object scatter, the system derives the material attenuation at any energy based on the signal from two relative regions of photon energy from the spectrum: the low-energy and the high-energy portions of the incident x-ray spectrum.

Such systems may use a direct conversion detector material in lieu of a scintillator. One of the ESCT, MECT, and/or DECT imaging systems in an example is configured to be responsive to different x-ray spectra. Energy sensitive detectors may be used such that each x-ray photon reaching the detector is recorded with its photon energy. One technique to acquire projection data for material decomposition includes using energy sensitive detectors, such as a CZT or other direct conversion material having electronically pixelated structures or anodes attached thereto. However, such systems typically include additional cost and complexity of operation in order separate and distinguish energy content of each received x-ray photon.

In an alternative, a conventional scintillator-based third-generation CT system may be used to provide energy sensitive measurements. Such systems may acquire projections sequentially at different peak kilovoltage (kVp) operating levels of the x-ray tube, which changes the peak and spectrum of energy of the incident photons comprising the emitted x-ray beams. A principle objective of scanning with two distinctive energy spectra is to obtain diagnostic CT images that enhance information (contrast separation, material specificity, etc.) within the image by utilizing two scans at different polychromatic energy states.

One technique has been proposed to achieve energy sensitive scanning including acquiring two scans at, for instance, 80 kVp and 140 kVp. The two scans may be obtained (1) back-to-back sequentially in time where the scans require two rotations of the gantry around the subject that may be hundreds of milliseconds to seconds apart, (2) interleaved as a function of the rotation angle requiring one rotation around the subject at each kVp, or (3) using a two tube/two detector system with the tubes/detectors mounted ~90 degrees apart, as examples.

However, such systems may be prone to image quality issues and/or have costs associated therewith. For instance, in the first example (1), when two scans, at low and high energy, are obtained back-to-back sequentially in time, the "hundreds of milliseconds to seconds" separation in time between the two scans can cause image artifacts and blurring due to patient motion and registration errors. Also, the scan typically takes 2× the amount of time compared to a conventional monochromatic imaging session, and the amount of radiation dose can be significantly increased because the two sets of data are acquired at each relative axial location. In the second example (2), when interleaving, system capacitance and other factors can cause a reduced amount of energy separation to occur during the rapid alternation between low and high energy states. That is, although example (2) may be desirable for a number of reasons (rapid data acquisition, low dose, shortened scanning sessions, and low cost, as examples), desired energy separation between low and high may not be obtained because the system may not reach its desired energy state in the short period of time before the system is triggered to switch to the next energy state. In the third example (3), a two tube/two detector system tend to be prohibitively expensive. And registration of high and low energy scans also can result in misregistration due to the time lapse between the first and second tube scanning, leading to image artifacts and blurring.

Thus, there is a need to acquire dual or multi-energy data having little or no data misregistration between high and low energy shots, and in a cost-competitive fashion. It would therefore be desirable to design a system and method for acquiring multi-energy data for material decomposition.

BRIEF DESCRIPTION

According to an aspect of the invention, a CT system includes a rotatable gantry having an opening to receive an object to be scanned, an x-ray source configured to emit x-rays toward the object from a first focal spot location and from a second focal spot location, a detector configured to detect x-rays passing through the object, wherein the detector comprises a plurality of detector pixels configured to output signals indicative of the detected x-rays, a grating collimator positioned between the x-ray source and the detector, the grating collimator comprised of alternating first and second materials, a controller configured to emit a first beam of x-rays from the first focal spot and to a first detector pixel, wherein the first beam of x-rays passes along a ray and through one of the first materials of the grating collimator, and subsequently emit a second beam of x-rays from the second focal spot and to the first detector pixel, wherein the second beam of x-rays passes substantially along the ray and through one of the second materials of the grating collimator, and a computer programmed to generate a first kVp image dataset using data acquired from the first beam of x-rays and from the first detector pixel, generate a second kVp image dataset using data acquired from the second beam of x-rays and from the first detector pixel, and reconstruct a basis material image of the object using the first kVp image dataset and the second kVp image dataset.

According to another aspect of the invention, a method of CT imaging includes emitting a first beam of x-rays from a first focal spot toward a first pixel of a CT detector, passing the first beam of x-rays through a first region of a grating collimator and along a ray through a patient, emitting a second beam of x-rays from a second focal spot toward the first pixel, passing the second beam of x-rays through a second region of the grating collimator and substantially along the ray through the patient, acquiring a first kVp image dataset using the first pixel when the first beam of x-rays is emitted thereto from the first focal spot, acquiring a second kVp image dataset using the first pixel when the second beam of x-rays is emitted thereto from the second focal spot, and generating a basis material image of the patient using the first kVp image dataset and the second kVp image dataset.

According to yet another aspect of the invention, a computer readable storage medium having a computer program stored thereon representing a set of instructions that when executed by a computer causes the computer to, emit a first beam of x-rays from a first focal spot to a first detector pixel of a CT detector, wherein the first beam of x-rays passes along a ray and through a first region of a grating collimator, emit a second beam of x-rays from a second focal spot to the first detector pixel, wherein the second beam of x-rays pass substantially along the ray and through a second region of the grating collimator, acquire a first kVp image dataset using data acquired from the first beam of x-rays emitted toward the first detector pixel, acquire a second kVp image dataset using data acquired from the second beam of x-rays emitted toward the first detector pixel, and reconstruct a basis material image of the object using the first kVp image dataset and the second kVp image dataset.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy.

The operating environment of embodiments of the invention is described with respect to a sixty-four-slice computed tomography (CT) system. However, it will be appreciated by those skilled in the art that embodiments of the invention are equally applicable for use with other multi-slice configurations. Moreover, embodiments of the invention will be described with respect to the detection and conversion of x-rays. One skilled in the art will further appreciate that embodiments of the invention are equally applicable for the detection and conversion of other high frequency electromagnetic energy. Embodiments of the invention will be described with respect to a "third generation" CT scanner, but is equally applicable with other CT systems.

An MECT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

Figure 1:
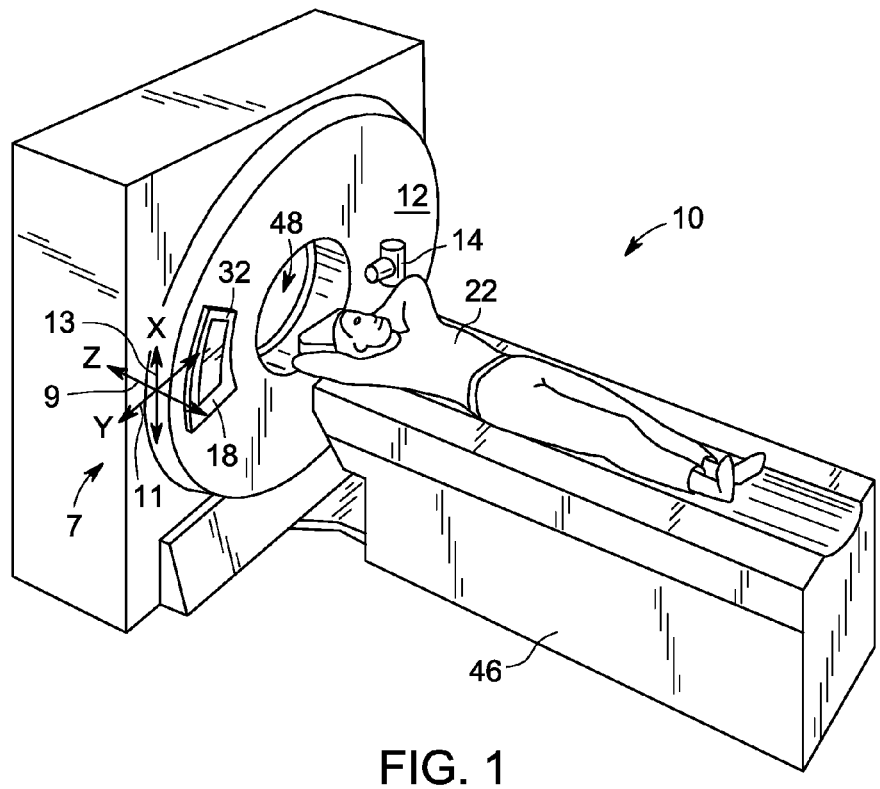
FIG. 1 is a pictorial view of a CT imaging system.
Figure 2:
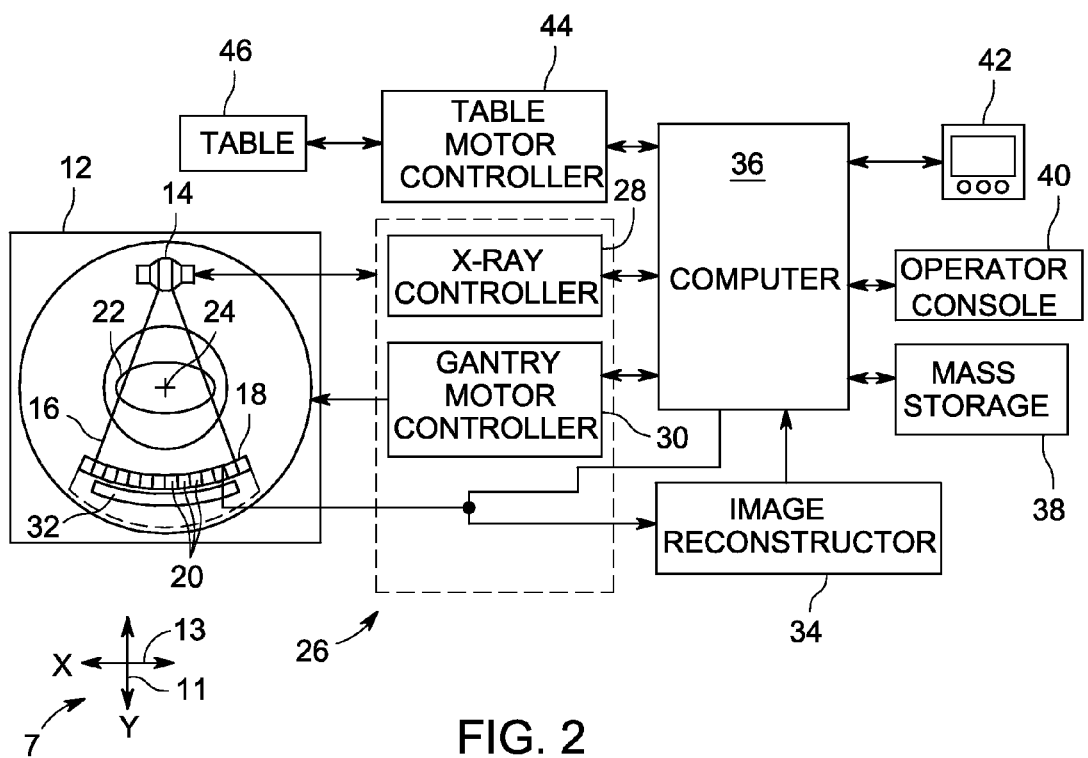
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

FIGS. 1 and 2 illustrate a triad 7 that defines a coordinate system relative to rotatable components on gantry 12, such as detector assembly 18 and x-ray source 14. Triad 7 defines a z-axis 9 that corresponds generally to an axial length of patient 22 as well as center of rotation 24. Z-axis 9 also defines what is commonly referred to as a slice direction of system 10. Triad 7 also includes y-axis 11 that generally represents a radial direction that passes from x-ray source 14 and detector assembly 18, and is also a path generally along which x-rays 16 pass from source 14 to assembly 18. X-axis 13 extends generally in a circumferential direction of gantry 12. That is, x-axis 13 extends generally in the rotational direction of components mounted on gantry 12 that include source 14 to assembly 18.

Figure 3:
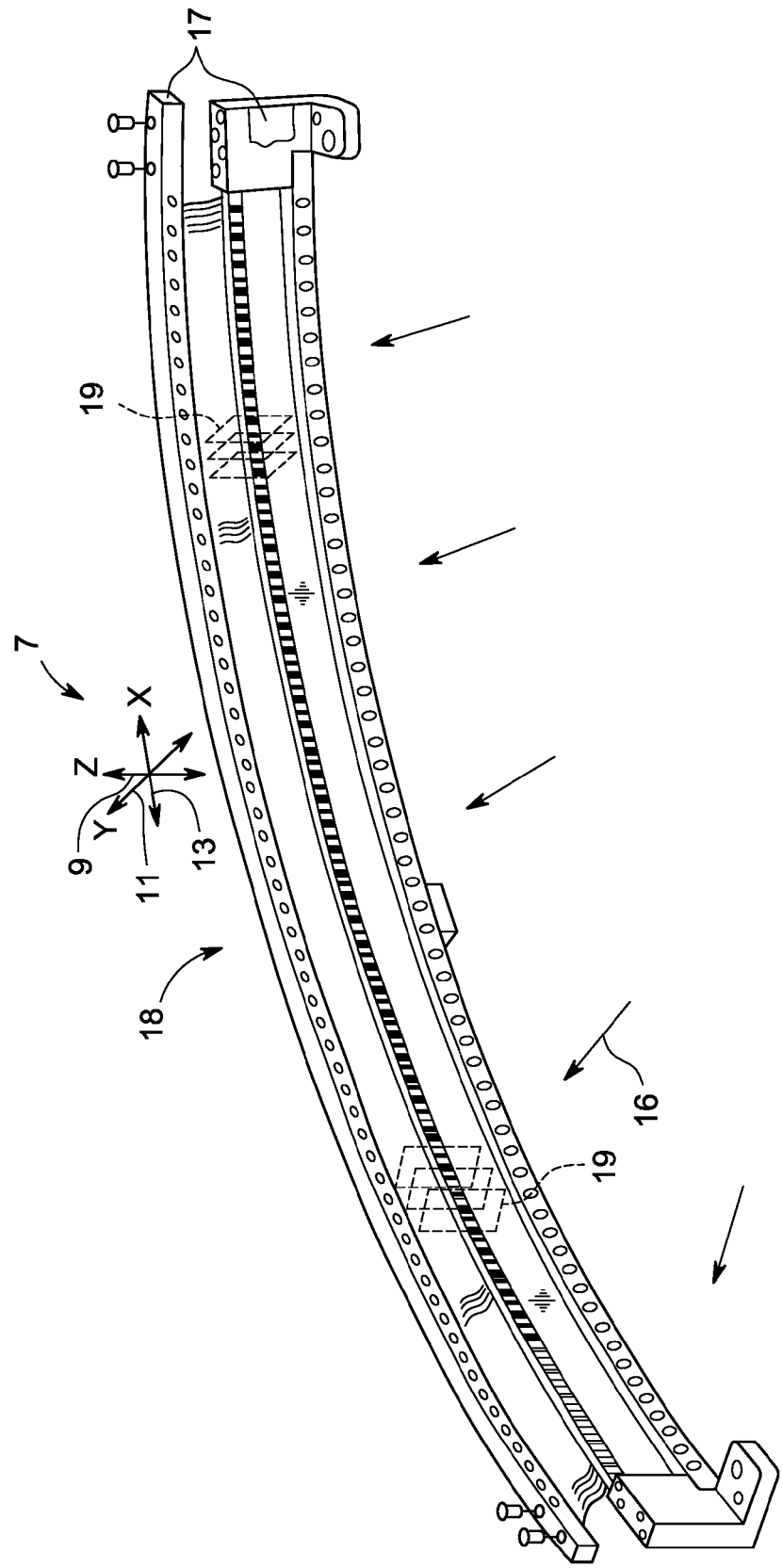
FIG. 3 is a perspective view of one embodiment of a CT system detector array.

As shown in FIG. 3, detector assembly 18 includes rails 17 having anti-scatter or collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
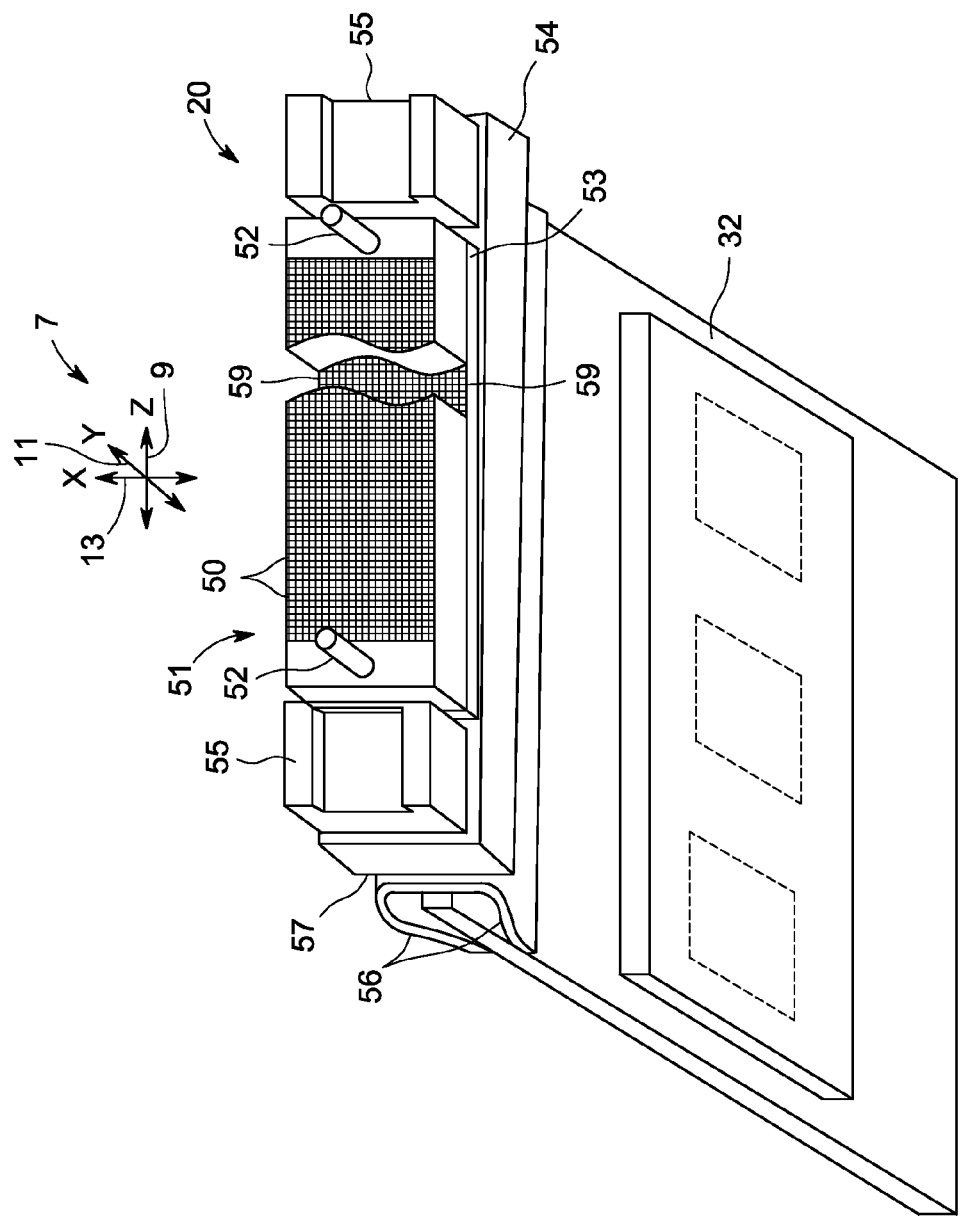
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59 and is a scintillator material that, as known in the art, generates photons when impinged by a high-energy photon such as an x-ray. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52. Consistently, triad 7 as described above is also illustrated in FIGS. 3 and 4 and illustrates z-axis 9, y-axis 11, and x-axis 13. In an alternate embodiment, detector 20 includes, in lieu of scintillator pack 51 and backlit diode array 53, an energy sensitive detector configured to discriminate energy content of impinging x-rays and/or count impinging photons.

In the operation of the illustrated scintillator embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Generally, in MECT or DECT, multiple sets of measurements are acquired at different respective mean energies. This provides more information to resolve the energy-dependence of the attenuation process and thereby enhance contrast between different materials, virtually emphasize or eliminate some specific materials, and eliminate artifacts induced due to spectral shifts (beam hardening). In particular, MECT may be used, for example, to acquire data at high, low, and intermediate x-ray tube voltages. MECT can also be desirable in the case where more than 3 independent energy basis functions are present and need to be discerned, such as in the presence of materials with K-edges.

The measurements at two different energy spectra $S_L(E)$ and $S_H(E)$ are given by:

$$I_L = \int S_L(E) \exp(-\int \mu(r,E) dr) dE$$

$$I_H = \int S_H(E) \exp(-\int \mu(r,E) dr) dE \quad \text{(Eqn. 1)}$$

where μ is the linear attenuation coefficient at energy E and location r.

Typically, μ is decomposed into two (or more) basis materials:

$$\mu(r,E) = a(r) A(E) + b(r) B(E) \quad \text{(Eqn. 2)}$$

where a(r) and b(r) are the spatially varying coefficient, and A(E) and B(E) are the energy dependencies of the respective basis materials.

Similarly, the line integral of the attenuation can be decomposed as:

$$\int \mu(r,E) = A(E) \int a(r) + B(E) \int b(r) = A(E) p_a + B(E) p_b \quad \text{(Eqn. 3)}$$

where $p_a$ and $p_b$ are the basis material line integrals.

The set of measurements from Eqn. 1 may thus be rewritten as:

$$I_L = f_L(p_a, p_b)$$

$$I_H = f_H(p_a, p_b) \quad \text{(Eqn. 4)}.$$

The functions $f_L$ and $f_H$ can be determined empirically, based on calibration measurements of different material combinations with spectra $S_L$ and $S_H$, after which $p_a$ and $p_b$ can be computed by inverting the set of equations of Eqn. 4.

In one embodiment, it may be preferred to directly define the inverse functions $g_a$ and $g_b$ from the calibration experiments, resulting in the following material decomposition (MD) step:

$$p_a = g_a(I_L, I_H)$$

$$p_b = g_b(I_L, I_H) \quad \text{(Eqn. 5)}.$$

A reconstruction algorithm is used to reconstruct a(r) and b(r) based on sinograms $p_a$ and $p_b$, respectively. The reconstruction algorithm can be a direct algorithm (such as filtered backprojection) or an iterative algorithm (such as penalized weighted least squares with ordered subsets or iterative coordinate descent). In these cases, the input to the reconstruction algorithm are sinograms $p_a$ and $p_b$ obtained from Eq. 5.

In an alternative, the entire inversion process may be set up as one iterative reconstruction process with unknowns a(r) and b(r), and using as inputs the measurements $I_L$ and $I_H$, and with the forward model given by Eqn. 1.

Embodiments of the invention start from a first reconstruction of the basis materials and improve those reconstructed images by incorporating knowledge of the noise in the measurements and prior knowledge on the images.

Figure 5:
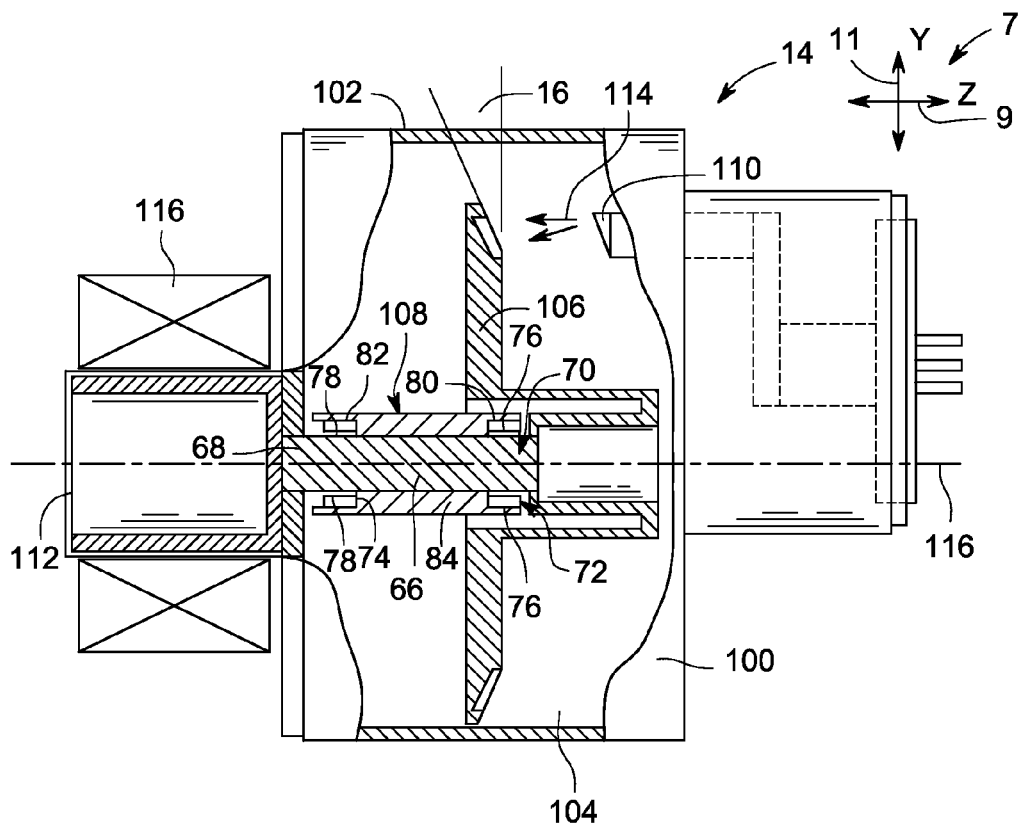
FIG. 5 is an x-ray tube that may be incorporated into embodiments of the invention.

FIG. 5 illustrates a cross-sectional view of an exemplary x-ray tube 14 that can be incorporated into embodiments of the present invention. X-ray tube 14 includes a casing 100 having a radiation emission passage 102 formed therein. Casing 100 encloses a vacuum 104 and houses an anode 106, a bearing assembly 108, a cathode 110, and a rotor 112. Electrons 114 are caused to emit from a filament within cathode 110 toward anode 106, as commonly understood in the art. X-rays 16 are produced when electrons 114 are suddenly decelerated when directed from cathode 110 to anode 106 via a potential difference therebetween of, for example, 60 thousand volts or more in the case of CT applications. X-rays 16 are emitted through radiation emission passage 102 toward a detector array, such as detector array 18 of FIGS. 2 and 3. A stator 116 drives rotor 112, which rotationally drives anode 106. To avoid overheating anode 106 from electrons 114, anode 106 is rotated at a high rate of speed about a centerline 118 at, for example, 90-250 Hz.

Figure 6:
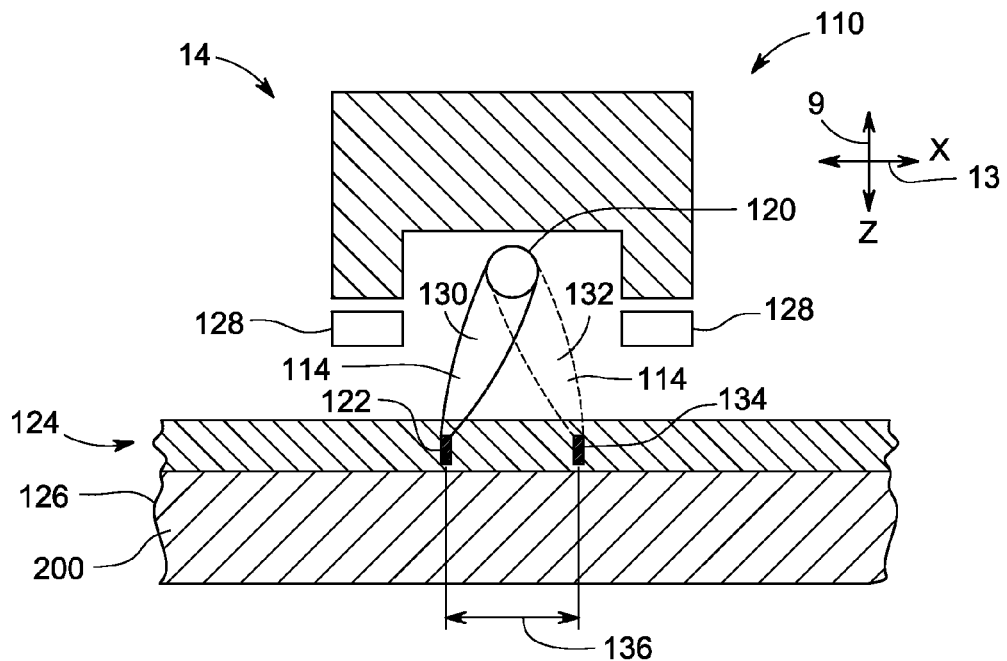
FIG. 6 is a schematic view of an x-ray tube having a cathode with one filament according to embodiments of the invention.

According to embodiments of the invention, focal spot flying (also known in the art as 'focal spot wobble') may be implemented in x-ray tube 14. Referring now to FIG. 6, components of x-ray source 14 are shown as including cathode 110 having a filament 120. Beam of electrons 114 is emitted from filament 120 to a first focal spot 122 on anode 106 of x-ray source 14. Anode 106 includes a beveled surface 124 positioned on a base 126 of anode 106. Beam of electrons 114 is electromagnetically or electrostatically deflected by the use of a pair of electrodes 128 having beam of electrons 114 passing therethrough. By applying an electromagnetic or electrostatic field to electrodes 128, beam of electrons 114 emits along path 130 to the position of first focal spot 122. Beam of electrons 114 may likewise be directed along a second path 132 to the position of a second focal spot 134 on anode 106 by appropriately altering the electromagnetic or electrostatic field. Accordingly, beam of electrons 114 emitted from a single filament 120 may be rapidly wobbled, up to several kHz or more and approximately 5 kHz in one embodiment, along x-direction 13 to impinge upon anode 106 at focal spots 122, 134 by altering the field applied to pair of electrodes 128. X-rays 16 therefore can be caused to emit from two focal spots 122, 134 and emit toward detector assembly 18 (i.e., in Y-direction 11, out of the page in FIG. 6), as illustrated in FIGS. 1 and 2, having a separation 136 therebetween. Multi-energy imaging data can be obtained by rapidly alternating the source energy between a low kVp and a high kVp, as known in the art.

Figure 7:
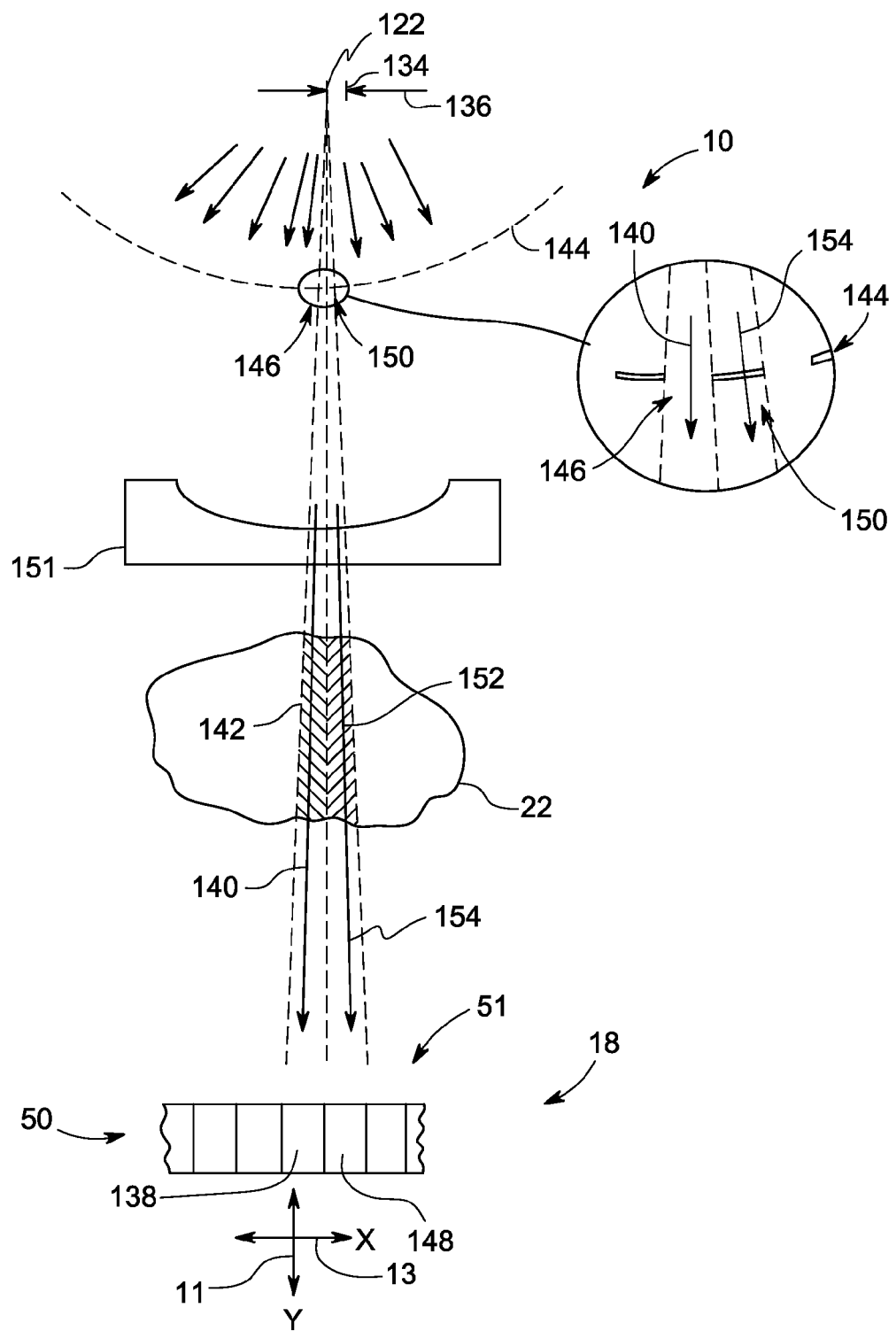
FIG. 7 is a graphical representation of elements of a CT system, according to one embodiment of the invention.

According to the invention, multi-energy imaging data may be acquired that utilizes the focal spot flying (i.e., wobble) technique coupled with a grating collimator. Referring to FIG. 7, a graphical representation of elements of system 10 is illustrated according to an embodiment of the invention. System 10 of FIG. 7 includes focal spots 122, 134 corresponding to that described with respect to FIG. 6 above that emanate from x-ray tube 14. X-rays 16 are illustrated emitting from focal spot 122 and fan out therefrom toward patient 22. However, as stated above, x-rays 16 also emit from focal spot 134 when electrons 114 of x-ray tube 14 are caused to wobble during operation thereof. X-rays 16 impinge upon detector assembly 18, some pixels 50 of which are illustrated in pack 51.

X-rays 16 that emanate from first focal spot 122 and fall upon a pixel 138 are illustrated. As illustrated, pack 51 includes pixels 50 that extend along x-direction 13, and in an array of 57 packs along an arc, as illustrated above with respect to FIG. 3. Consistent with detector 20 illustrated above in FIG. 4, pixels also extend along z-direction 9 (not illustrated in FIG. 7, extending in and out of the page). Thus, x-rays 16 that pass along a first ray 140 pass through a first volume 142 of patient 22 and fall upon pixel 138. X-rays 16 passing along ray 140 also pass through a grating collimator 144. Grating collimator 144 includes an alternating array of materials that have either a first amount of x-ray filtration or a second amount of x-ray filtration associated therewith. That is, grating collimator 144 has materials positioned therein, and is itself positioned within system 10 accordingly, such that x-rays pass through a first material or region 146 when x-rays 16 are caused to emit from first focal spot 122, through first volume 142, and toward pixel 138. Simultaneously, x-rays 16 that emit from first focal spot 122 and fall upon a neighboring pixel 148 pass through a second material or region 150 of grating collimator 144, and also pass through a second volume 152 along a second ray 154.

Figure 8:
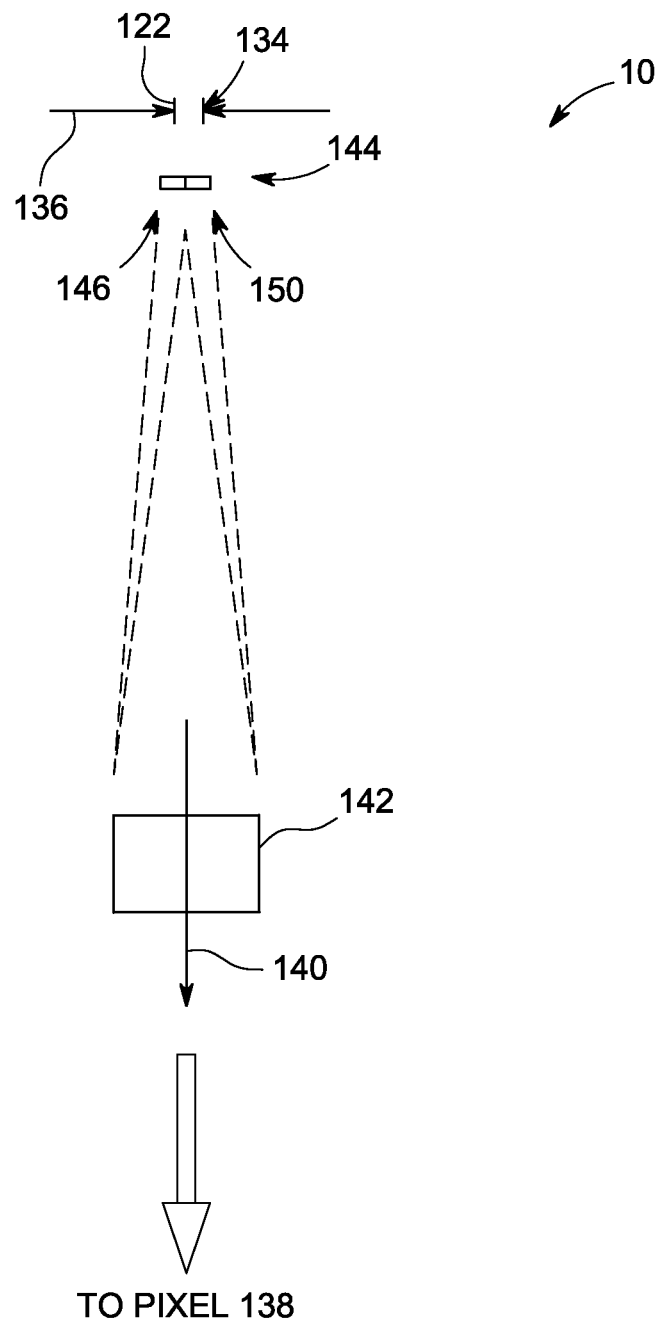
FIG. 8 is a representation of CT system elements for data acquired at a pixel that emits from two focal spots.

Thus, referring to FIGS. 7 and 8, x-rays 16 passing to pixel 138 from first focal spot 122 as a first beam of x-rays pass through first volume 142 and are filtered by first material or region 146. X-rays 16 simultaneously passing to neighboring pixel 148 through second volume 152 are filtered by second material or region 150. When x-rays 16 are subsequently caused to emit from second focal spot 134 as a second beam of x-rays, the second beam of x-rays that passes through first volume 142 and toward pixel 138 are filtered by second material or region 150 and, because separation 136 is small relative to the overall gantry geometry and because the rate of 'wobble' from first focal spot 122 to second focal spot 134 is quite rapid, first and second beams passing to pixel 138 follow substantially the same ray 140. As such, x-rays impinging upon pixel 138 having emitted from focal spot 122 and passing through first material 146 are at a first energy level, and x-rays impinging upon pixel 138 having emitted from focal spot 134 and passing through second material 150 are at a second level, the amount of energy separation therebetween being dependent on the differing amounts of filtration provided by materials 146, 150.

In this example, first material or region 146 is an opening or aperture and presents no additional filtration beyond that of air. However, embodiments of the invention may include a solid material for first material or region 146 instead of an aperture, having a material that is, in one embodiment, different from second material 150. In another embodiment, first material or region 146 is the same material as that of second material or region 150, but having a different material thickness so as to present a different filtration between the two regions 146, 150. Second material or region 150 in this example is a material providing a relatively high degree of x-ray filtration such as tungsten. In one embodiment the tungsten in region is 0.06 mm in thickness, but may range below or above this thickness depending on desired filtration amount, x-ray energy, and the like, as known in the art. Grating collimator 144 includes a repeating array of first material or region 146 and second material or region 150, the pattern of which corresponds geometrically with the pattern of pixels 50 in pack 51, and extending along x-direction 13 through the channels of detector 20.

In conjunction with wobbling or flying the focal spot from focal spots 122, 134, x-ray controller 28 may cause fast kV switching between, for instance, 80 KeV and 140 KeV, in order to obtain low and high energy data. That is, when electrons are emitted along path 130 to focal spot 122, 80 KeV and then 140 KeV may be applied, and when electrons are rapidly switched to and are emitted along path 132 to focal spot 134, 80 KeV and then 140 KeV may be applied. In an alternate embodiment, a high KeV (140 KeV, for instance) may be applied from both focal spot locations 122, 134 and then a low keV (80 KeV, for instance) may be applied from both focal spot locations 122, 134.

Figure 9:
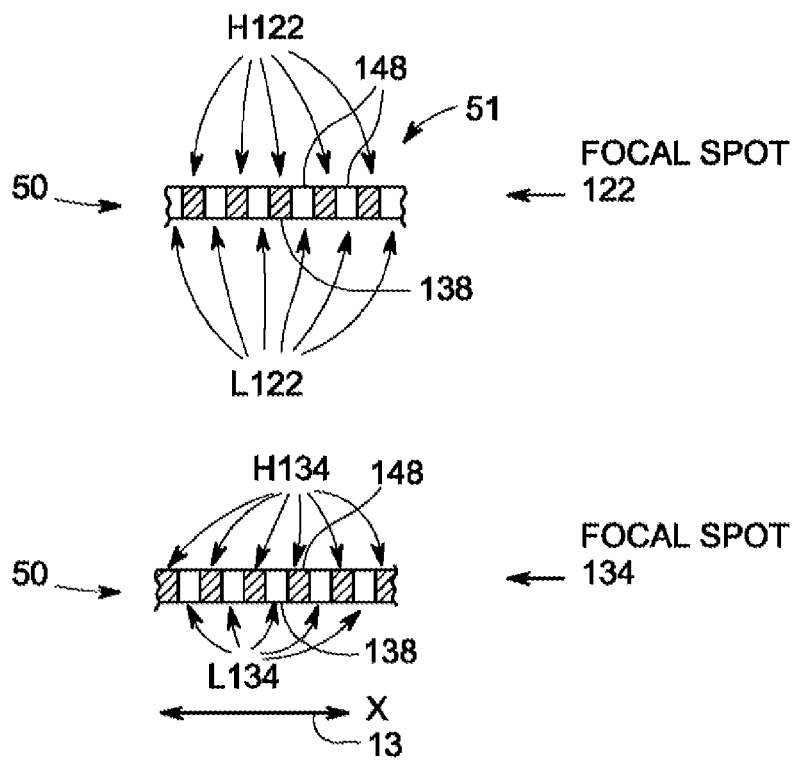
FIG. 9 illustrates pixel arrays for obtaining alternating high and low kVp data from a CT system, according to an embodiment of the invention.

FIG. 9 illustrates several of pixels 50 from pack 51, and it is to be understood that the illustrated pixels only represent a few of many pixels along x-direction 13 of detector 20 and along detector assembly 18 as illustrated in FIG. 3. Referring to FIG. 9, pixels 50 are illustrated to highlight which pixels receive 'high kVp' data and which pixels receive 'low kVp' data, and corresponding to a respective focal spot source (either 122 or 134, in this example). When x-rays 16 emit from focal spot 122, those x-rays 16 passing through first volume 142 and along first ray 140 are not attenuated as they pass through first region 146 of grating collimator 144, and thus represent a high kVp acquisition. Those pixels corresponding to the 'high kVp' portion of the acquisition are designated as 'H122' to illustrate high kVp data obtained from focal spot 122 and having passed through first material or region 146. Data obtained for the high kVp acquisition will thus be obtained in every other pixel extending in x-direction 13 from pixel 138 because of the alternating structure of grating collimator 144. Pixels corresponding to the 'low kVp' portion of the acquisition are designated as 'L122' to illustrate low kVp data obtained from focal spot 122 and having passed through second material or region 150, having an alternating pattern as well.

Likewise, when x-rays 16 emit from focal spot 134, those x-rays 16 passing through volume 142 also pass substantially along ray 140 but are attenuated as they pass through second material or region 150 of grating collimator 144, and thus represent additional data for the low and high kVp acquisition to augment that acquired from focal spot 122. That is, because separation 136 is small (perhaps a few hundred microns) compared to the scale of system 10, x-rays 16 that pass to pixel 138 along first ray 140 also pass along substantially the same ray 140 when emitted from second focal spot 134. Therefore, pixel 138 acquires high kVp image data from x-rays emitted from focal spot 122 and, once wobbled to second focal spot 134, pixel 138 acquires low kVp data a very short time later just after the wobble occurs.

Thus, pixels corresponding to the 'high kVp' portion of the acquisition are designated as 'H134' to illustrate high kVp data obtained from focal spot 134 and having passed through first material or region 146. Pixels corresponding to the 'low kVp' portion of the acquisition are designated as 'L134' to illustrate low kVp data obtained from focal spot 134 and having passed through second material or region 150. The data acquired from the two subsequent acquisitions thus augment one another. High kVp pixel data from pixels 'H122' derived from focal spot 122 is augmented with high kVp pixel data from pixels 'H134' derived from focal spot 134. Likewise, low kVp pixel data from pixels 'L122' derived from focal spot 122 is augmented with low kVp pixel data from pixels 'L134' derived from focal spot 134. As such, a first kVp image dataset is generated using the first beam of x-rays and the second beam of x-rays, and a second kVp image data set is likewise generated using the first beam of x-rays and the second beam of x-rays. That is, high and low kVp datasets are obtained by obtaining high and low kVp data interspersed during the two acquisitions (focal spots 122 and 134) as illustrated in FIG. 9, and combining them respectively to form a high kVp dataset and a low kVp dataset.

As such, by causing electrons 114 to wobble to form two focal spot locations 122 and 134 that are separated along x-direction 13, passing emitted x-rays 16 therefrom through grating collimator 144 enables complete sets of both high and low kVp data to be obtained having energy separation that results from passing through filtration materials 146, 150. By combining the high kVp datasets corresponding to 'H122' and 'H134' from the two respective focal spot locations 122, 134, high kVp data can be obtained for x-rays having passed through all volumes (representatively 142 and 152) of patient 22. And, by combining the low kVp datasets corresponding to 'L122' and 'L134' from the two respective focal spot locations 122, 134, high kVp data can be obtained for x-rays having passed through all volumes as well (representatively 142 and 152) of patient 22.

Thus, because physical separation 136 is small relative to pixel size and overall system geometry, and because the rate of wobble (several kHz or more) is very rapid relative to the rotation rate of the gantry, one skilled in the art will recognize that components and dimensions, being sized accordingly, can be designed in order that first ray 142 is substantially traced to pixel 138 for x-rays passing from both focal spots 122, 134, and likewise for rays passing to the other pixels 50. Thus, according to the invention, by causing the focal spot to wobble along the x-direction or rotational direction of the components on the gantry, both high and low kVp data can be acquired within each rotation of the gantry, by alternatively passing the x-rays through a first filter and a second filter of grating collimator 144 and with a single source kVp. One skilled in the art will recognize also that additional energy separation between acquired data can be obtained by rapidly alternating the source kVp in conjunction with wobble. In the example above, high kVp imaging data may be acquired when passing a high kVp energy, such as 140 KeV, through materials 150 of grating collimator 144 and then subsequently low kVp imaging data may be acquired when passing low kVp energy, such as 80 KeV, through materials 146 of grating collimator 144 (air in this example). Thus, although energy separation can be obtained by wobbling x-rays having a single polychromatic energy as discussed, additional energy separation can be obtained by also alternating the source kVp from high to low in conjunction with the wobble to obtain yet greater energy separation in the imaging data.

As such, a new multi-energy imaging scheme which utilizes the focal spot flying technique coupled with a grating collimator is disclosed. The focal spot flying technique is used to image a patient using single polychromatic X-ray spectrum (such as a 140 kVp polychromatic spectrum) or dual-energy spectra (at 80 kVp and 140 kVp, as an example). A grating collimator is designed to facilitate the filtering and the separation of the X-ray energy spectrum. Effectively with the focal spot flying and as described, the patient is imaged at different energy spectrums. Thus, with this approach, each set of the low and high energy views can be considered as acquired at the same spatial location simultaneously. Thus projection spaced image decomposition can be readily applied which can result in beam hardening artifact reduction or elimination.

According to the invention, a grating collimator is designed accordingly and installed on the rotation gantry between the source and the patient. To realize dual-energy, the focal spot flying distance (D) (separation 136 in FIG. 6) between the two positions should satisfy the following condition:

$$D = N*(SID/IDD)*Sdet, \quad \text{(Eqn. 6)}.$$

where N is an integer larger than 0. SID is designated as the source-to-isocenter (ISO) distance. IDD is the ISO to detector distance. Sdet is the physical size of one detector element in the focal spot flying direction (i.e, x-direction 13).

Two different materials are utilized for the grating collimator for dual-energy imaging. In the example provided above, one of the "materials" is air and other is tungsten. The length (L) of each material grating (i.e., the length of each material 146, 150 along x-direction 13) is determined as following:

$$L = N*(SGD/SDD)*Sdet, \quad \text{(Eqn. 7)}.$$

where SGD is the source-to-grating distance and SDD is the source to detector distance.

With focal spot flying at the designated fixed distance, the object is imaged at the same spatial location with two different X-ray spectrums, which are achieved by filtering the incident polychromatic spectrum with two different collimation materials. Due to the focal spot flying and the attenuation through each material 146, 150, the same ray path through the patient are from different energy spectrums between the two adjacent views.

After the data are acquired, the projection rays filtered by material 146 are grouped together which forms the first energy data, and the projection rays filtered by material 150 are grouped together to form the second energy data. As stated, the data may be acquired using a single energy at each focal spot location, or energy may be altered from high to low in conjunction with the wobble of the focal spot. In this fashion, the invention supports at least the following scenarios:

a. Fast kVp switching coupled with focal spot flying. That is, at high kVp setting, acquire two images at two different focal spot positions. At a low kVp setting, acquire two images at two different focal spot positions. Thus for 1s rotation speed, image data may be acquired at ~4000 views per rotation.

b. Fast kVp switching with focal spot flying just during the high kVp acquisition, which can further separate the overlap between the high and low kVp spectrum.

The material decomposition process may be conducted in the projection space or image space to generate basis material images and various monochromatic images with different energies. It is noted that a body bowtie filter may be included, according to the invention. Thus, referring back to FIG. 7, an optional bowtie filter 151 is illustrated that may be used in conjunction with grating collimator 144, according to the invention. And, although bowtie filter 151 is illustrated as positioned between grating collimator 144 and object 22, it is also contemplated in another embodiment that bowtie filter 151 can be positioned between x-ray tube 14 (having focal spots 122/134) and grating collimator 144 as well. The above discussion assumes an in-plane focal spot flying is used. That is, it is assumed that focal spot wobble occurs along x-direction 13 as illustrated in FIG. 6. However, it is contemplated that this disclosure can work with a flying spot in any flying direction, including in-plane (i.e., x-direction 13), along a z-direction (i.e., z-direction 9) or in a diagonal direction (along both x and z-directions). Thus, in an alternate embodiment when the flying direction is in a z-direction, image may be acquired according to that illustrated in FIG. 8, with the offset 136 corresponding instead to a z-direction. In addition, in an embodiment that includes a diagonal wobble in both an x and a z-direction, FIG. 8 also illustrates data acquired according to this embodiment, however, separation 136 occurs in one of the orientations and separation in and out of the page of the illustrated figure also occurs simultaneously.

Air and tungsten were used in the above example, but depending on the energy range, different materials can be selected based on their k-edge and density and can be combined to create this effect at selected energy ranges in the spectrum. Also, a filter made with a single element can be improved through the use of multiple materials to allow for more controlled shaping of the energy spectrum. This allows to selectively choose a region of the spectrum that is affected, enabling the attenuation to be 'tuned,' which potentially can lead to a more robust multi-energy imaging system.

Thus, according to the invention, a relatively easy and non-expensive system and method, which utilizes the focal spot flying technique and grating collimation for multi-energy CT imaging, can be implemented.

Figure 10:
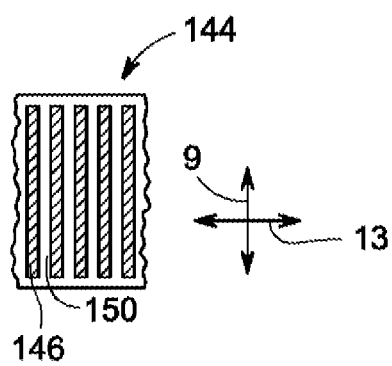
FIG. 10 shows a portion of a grating collimator, having alternating grates along an x-direction of a CT system.
Figure 11:
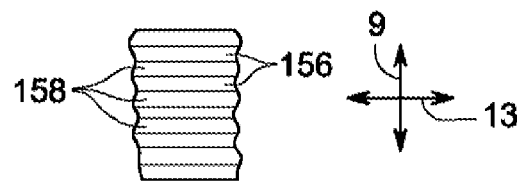
FIG. 11 shows a portion of a grating collimator, having alternating grates along a z-direction of a CT system.

Furthermore, although the above discussion is directed toward focal spot flying or wobble along x-direction 13, it is contemplated that the invention disclosed herein may be applied along z-direction 9 as well. That is, in a implementation in which focal spot offset is along z-direction 9 instead of x-direction 13, a grating collimator may be implemented that similarly provides low and high x-ray attenuation along z-direction 9. Referring back to FIG. 7, for example, grating collimator 144 extends in a generally circumferential direction and thus, along z-direction the attenuation is constant. See for instance FIG. 10 showing a portion of grating collimator 144. FIG. 10 shows first material or region 146 (as an opening) and second material or region 150, both extending along z-direction 9. As such, according to the invention, grating collimator 144 is comprised of a grid or grating of alternating materials. However, in the alternate embodiment in which a focal spot is instead offset or wobbled in z-direction 9, the gridding is likewise provided along the alternate axis as illustrated in FIG. 11 having alternating first materials 156 and second materials 158 alternating along z-direction 9. And, although only a few of the total number of z-grids are illustrated, it is contemplated that the number of z-grid materials 156, 158 corresponds, in one embodiment, to the number of slices in system 10, for instance 4, 16, or 64, as examples.

Figure 12:
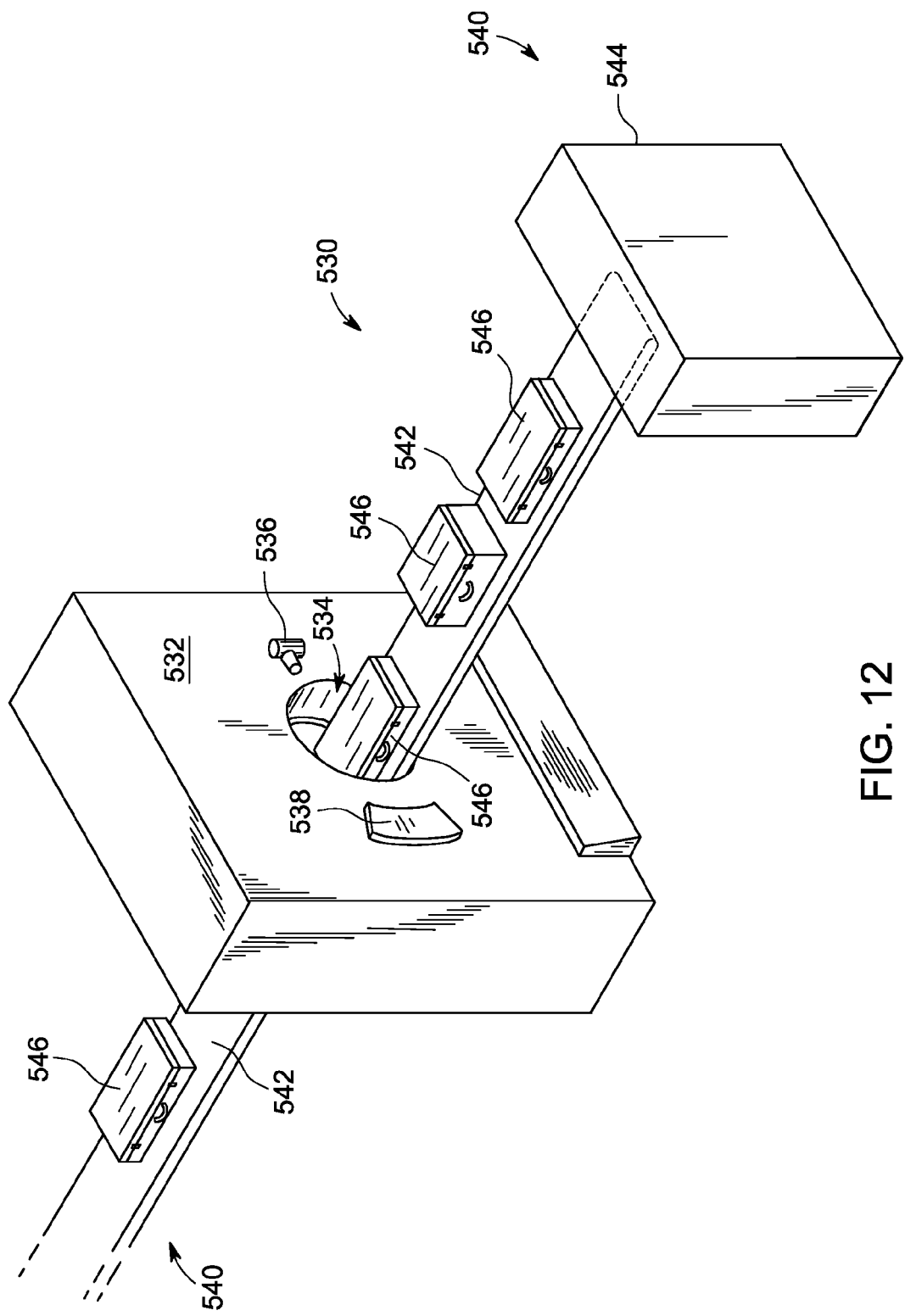
FIG. 12 is a pictorial view of a CT system for use with a non-invasive package inspection system.

Referring now to FIG. 12, package/baggage inspection system 530 includes a rotatable gantry 532 having an opening 534 therein through which packages or pieces of baggage may pass. The rotatable gantry 532 houses a high frequency electromagnetic energy source 536 as well as a detector assembly 538 having scintillator arrays comprised of scintillator cells. A conveyor system 540 is also provided and includes a conveyor belt 542 supported by structure 544 to automatically and continuously pass packages or baggage pieces 546 through opening 534 to be scanned. Objects 546 are fed through opening 534 by conveyor belt 542, imaging data is then acquired, and the conveyor belt 542 removes the packages 546 from opening 534 in a controlled and continuous manner. As a result, postal inspectors, baggage handlers, and other security personnel may non-invasively inspect the contents of packages 546 for explosives, knives, guns, contraband, etc.

A technical contribution for the disclosed method and apparatus is that is provides for a computer implemented system and method of diagnostic imaging and, more particularly, to a system and method of acquiring multi-energy data for material decomposition.

One skilled in the art will appreciate that embodiments of the invention may be interfaced to and controlled by a computer readable medium having stored thereon a computer program. The computer readable medium includes a plurality of components such as one or more of electronic components, hardware components, and/or computer software components. These components may include one or more computer readable media that generally stores instructions such as software, firmware and/or assembly language for performing one or more portions of one or more implementations or embodiments of a sequence. These computer readable media are generally non-transitory and/or tangible. Examples of such a computer readable medium include a recordable data medium of a computer and/or storage device. The computer readable media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to an embodiment of the invention, a CT system includes a rotatable gantry having an opening to receive an object to be scanned, an x-ray source configured to emit x-rays toward the object from a first focal spot location and from a second focal spot location, a detector configured to detect x-rays passing through the object, wherein the detector comprises a plurality of detector pixels configured to output signals indicative of the detected x-rays, a grating collimator positioned between the x-ray source and the detector, the grating collimator comprised of alternating first and second materials, a controller configured to emit a first beam of x-rays from the first focal spot and to a first detector pixel, wherein the first beam of x-rays passes along a ray and through one of the first materials of the grating collimator, and subsequently emit a second beam of x-rays from the second focal spot and to the first detector pixel, wherein the second beam of x-rays passes substantially along the ray and through one of the second materials of the grating collimator, and a computer programmed to generate a first kVp image dataset using data acquired from the first beam of x-rays and from the first detector pixel, generate a second kVp image dataset using data acquired from the second beam of x-rays and from the first detector pixel, and reconstruct a basis material image of the object using the first kVp image dataset and the second kVp image dataset.

According to another embodiment of the invention, a method of CT imaging includes emitting a first beam of x-rays from a first focal spot toward a first pixel of a CT detector, passing the first beam of x-rays through a first region of a grating collimator and along a ray through a patient, emitting a second beam of x-rays from a second focal spot toward the first pixel, passing the second beam of x-rays through a second region of the grating collimator and substantially along the ray through the patient, acquiring a first kVp image dataset using the first pixel when the first beam of x-rays is emitted thereto from the first focal spot, acquiring a second kVp image dataset using the first pixel when the second beam of x-rays is emitted thereto from the second focal spot, and generating a basis material image of the patient using the first kVp image dataset and the second kVp image dataset.

According to yet another embodiment of the invention, a computer readable storage medium having a computer program stored thereon representing a set of instructions that when executed by a computer causes the computer to, emit a first beam of x-rays from a first focal spot to a first detector pixel of a CT detector, wherein the first beam of x-rays passes along a ray and through a first region of a grating collimator, emit a second beam of x-rays from a second focal spot to the first detector pixel, wherein the second beam of x-rays pass substantially along the ray and through a second region of the grating collimator, acquire a first kVp image dataset using data acquired from the first beam of x-rays emitted toward the first detector pixel, acquire a second kVp image dataset using data acquired from the second beam of x-rays emitted toward the first detector pixel, and reconstruct a basis material image of the object using the first kVp image dataset and the second kVp image dataset.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) system comprising:
   a rotatable gantry having an opening to receive an object to be scanned;
   an x-ray source configured to emit x-rays toward the object from a first focal spot location and from a second focal spot location;
   a detector that detects x-rays passing through the object, wherein the detector comprises a plurality of detector pixels that outputs signals indicative of the detected x-rays;
   a grating collimator positioned between the x-ray source and the detector, the grating collimator comprised of alternating first and second materials;

a controller that controls the CT system to perform the steps of:
  emitting a first beam of x-rays from the first focal spot and to a first detector pixel, wherein the first beam of x-rays passes along a ray and through one of the first materials of the grating collimator; and
  subsequently emitting a second beam of x-rays from the second focal spot and to the first detector pixel, wherein the second beam of x-rays passes substantially along the ray and through one of the second materials of the grating collimator; and
a computer that executes a program to further control the CT system to perform the steps of:
  generating a first kVp image dataset using data acquired from the first beam of x-rays and from the first detector pixel;
  generating a second kVp image dataset using data acquired from the second beam of x-rays and from the first detector pixel; and
  reconstructing a basis material image of the object using the first kVp image dataset and the second kVp image dataset.

2. The system of claim 1 wherein the computer further controls the CT system to perform the step of augmenting the first kVp image dataset using data acquired from the second beam of x-rays and from a second detector pixel that neighbors the first detector pixel.

3. The system of claim 1 wherein the controller controls the CT system to perform the step of emitting the first and the second beams of x-rays at substantially the same polychromatic energy.

4. The system of claim 3 wherein a peak polychromatic energy is approximately 140 kVp.

5. The system of claim 1 wherein the controller controls the CT system to perform the steps of emitting the first beam of x-rays at a first polychromatic energy, and emitting the second beam of x-rays at a second polychromatic energy that is different from the first energy.

6. The system of claim 1 wherein the first focal spot and the second focal spot are offset from one another along an x-direction of the rotatable gantry, the x-direction corresponding to a circumferential direction thereof.

7. The system of claim 6 wherein the grating collimator is positioned such that the first and second materials extend along the x-direction of the rotatable gantry.

8. The system of claim 1 wherein the computer further controls the CT system to perform the step of emitting the first beam of x-rays and the second beam of x-rays at the same energy potential.

9. The system of claim 1 wherein the computer further controls the CT system to perform the step of emitting the second beam of x-rays from a position that is offset from the first focal spot along an x-direction of the CT system, the x-direction corresponding to a circumferential direction of the CT system.

10. The system of claim 1 wherein the first material of the grating collimator is one of air and tungsten.

11. The system of claim 1 wherein the first and second focal spots are wobbled in one of an x-direction, a z-direction, and a diagonal x-z direction, wherein the x-direction corresponds to a circumferential direction of the rotatable gantry and the z-direction is perpendicular to the x-direction and is in a direction of an axis of rotation of the rotatable gantry.

12. The system of claim 1 wherein the grating collimator is positioned between the x-ray source and the object.

13. A method of computed tomography (CT) imaging comprising:
  emitting a first beam of x-rays from a first focal spot toward a first pixel of a CT detector;
  passing the first beam of x-rays through a first region of a grating collimator and along a ray through a patient;
  emitting a second beam of x-rays from a second focal spot toward the first pixel;
  passing the second beam of x-rays through a second region of the grating collimator and substantially along the ray through the patient;
  acquiring a first kVp image dataset using the first pixel when the first beam of x-rays is emitted thereto from the first focal spot;
  acquiring a second kVp image dataset using the first pixel when the second beam of x-rays is emitted thereto from the second focal spot; and
  generating a basis material image of the patient using the first kVp image dataset and the second kVp image dataset;
  wherein the grating collimator is comprised of a first material in the first region and a second material in the second region.

14. The method of claim 13 comprising:
  emitting the first beam of x-rays from the first focal spot toward a second pixel of the CT detector that neighbors the first pixel and through the second region of the grating collimator; and
  augmenting the second kVp image dataset with data acquired from the second pixel.

15. The method of claim 13 wherein the first and second beams of x-rays are emitted using substantially the same energy potential.

16. The method of claim 13 wherein emitting the second beam of x-rays from the second focal spot comprises emitting the second beam of x-rays from a position that is offset from the first focal spot along an x-direction of a CT system, the x-direction corresponding to a circumferential direction of the CT system.

17. The method of claim 13 wherein the first region of the grating collimator is one of air and tungsten.

18. The method of claim 17 wherein, when the first region of the grating collimator is tungsten, a thickness of the tungsten is approximately 0.06 mm.

19. The method of claim 13 wherein the first region of the grating collimator and the second region of the grating collimator are fabricated from the same material, and wherein the first region includes a first thickness of the same material and the second region includes a second thickness of the same material that is different from the thickness of the first material.

20. A non-transitory computer readable storage medium having a computer program stored thereon representing a set of instructions that when executed by a computer causes the computer to control a computed tomography (CT) system to perform the steps of:
  emitting a first beam of x-rays from a first focal spot to a first detector pixel of a CT detector, wherein the first beam of x-rays passes along a ray and through a first region of a grating collimator;
  emitting a second beam of x-rays from a second focal spot to the first detector pixel, wherein the second beam of x-rays pass substantially along the ray and through a second region of the grating collimator;
  acquiring a first kVp image dataset using data acquired from the first beam of x-rays emitted toward the first detector pixel;

acquiring a second kVp image dataset using data acquired from the second beam of x-rays emitted toward the first detector pixel; and reconstructing a basis material image of the object using the first kVp image dataset and the second kVp image dataset;

wherein the grating collimator is comprised of a first material in the first region and a second material in the second region.

21. The non-transitory computer readable storage medium of claim 20 wherein the computer is programmed to augment the first kVp image dataset using data acquired from the second beam of x-rays and from a second detector pixel that neighbors the first detector pixel.

22. The non-transitory computer readable storage medium of claim 20 wherein the instructions cause the computer to control the CT system to perform the step of emitting the first beam of x-rays and the second beam of x-rays toward the detector at the same energy potential.

23. The non-transitory computer readable storage medium of claim 20 wherein the instructions cause the computer to control the CT system to perform the step of emitting the first beam of x-rays from the first focal spot position, and subsequently emitting the second beam of x-rays from the second focal spot by electromagnetically deflecting a beam of electrons at a rate greater than 5 kHz.

* * * * *